US012594372B2

(12) United States Patent
Gordon

(10) Patent No.: US 12,594,372 B2
(45) Date of Patent: Apr. 7, 2026

(54) METHODS AND SYSTEMS FOR CONTROLLING ASPIRATION FLOW RATE

(71) Applicant: Alcon Inc., Fribourg (CH)

(72) Inventor: Raphael Gordon, Ladera Ranch, CA (US)

(73) Assignee: Alcon Inc., Fribourg (CH)

( * ) Notice: Subject to any disclaimer, the term of this patent is extended or adjusted under 35 U.S.C. 154(b) by 1812 days.

(21) Appl. No.: 16/691,675

(22) Filed: Nov. 22, 2019

(65) Prior Publication Data

US 2020/0164116 A1     May 28, 2020

Related U.S. Application Data

(60) Provisional application No. 62/771,282, filed on Nov. 26, 2018.

(51) Int. Cl.
*A61M 3/02* (2006.01)
*A61M 1/00* (2006.01)

(52) U.S. Cl.
CPC ............ *A61M 3/0208* (2014.02); *A61M 1/73* (2021.05); *A61M 1/74* (2021.05); *A61M 1/77* (2021.05); *A61M 3/0258* (2013.01); *A61M 2205/103* (2013.01); *A61M 2205/3334* (2013.01); *A61M 2205/3379* (2013.01); *A61M 2205/50* (2013.01)

(58) Field of Classification Search
CPC .. A61M 2205/3365; A61M 2205/3334; A61M 1/73; A61M 1/74; A61M 1/77; A61M 1/0023; A61M 1/0058; A61M 3/0283; A61F 9/007
See application file for complete search history.

(56) References Cited

U.S. PATENT DOCUMENTS

| | | | | | |
|---|---|---|---|---|---|
| 4,108,575 | A | * | 8/1978 | Schal | G05D 7/0676 |
| | | | | | 128/DIG. 13 |
| 5,733,257 | A | * | 3/1998 | Sternby | A61M 60/38 |
| | | | | | 604/27 |
| 6,447,441 | B1 | | 9/2002 | Yu | |
| 8,140,274 | B2 | * | 3/2012 | Gagel | F04B 43/1253 |
| | | | | | 702/50 |
| 8,790,096 | B2 | | 7/2014 | Sorensen | |
| 2002/0019607 | A1 | * | 2/2002 | Bui | A61F 9/00745 |
| | | | | | 604/67 |
| 2007/0217919 | A1 | * | 9/2007 | Gordon | F04B 49/20 |
| | | | | | 417/44.2 |

(Continued)

FOREIGN PATENT DOCUMENTS

| | | |
|---|---|---|
| GB | 2367594 B | 10/2002 |
| WO | 9219851 A2 | 11/1992 |

(Continued)

*Primary Examiner* — Jessica Arble
*Assistant Examiner* — Arjuna P Chatrathi
(74) *Attorney, Agent, or Firm* — PATTERSON + SHERIDAN, LLP

(57) ABSTRACT

Certain aspects of the present disclosure provide a surgical system comprising a pump motor configured to couple to a pump for pumping material through a probe, wherein the probe is connected to the pump through a connector. The surgical system also comprises a control module configured to determine a real-time flow rate through the probe and adjust a current pump rate of the pump to achieve a target flow rate, wherein the current pump rate is adjusted based on the real-time flow rate.

20 Claims, 3 Drawing Sheets

(56)         References Cited

U.S. PATENT DOCUMENTS

| | | | | |
|---|---|---|---|---|
| 2008/0114290 | A1* | 5/2008 | King | A61M 3/0201 |
| | | | | 604/30 |
| 2008/0125697 | A1* | 5/2008 | Gao | A61M 1/77 |
| | | | | 604/35 |
| 2013/0267779 | A1* | 10/2013 | Woolford | A61B 17/34 |
| | | | | 600/156 |
| 2015/0045712 | A1 | 2/2015 | Ninomiya et al. | |
| 2017/0049952 | A1* | 2/2017 | Jezierski | |
| 2017/0224888 | A1* | 8/2017 | Hickey | A61M 3/0279 |
| 2017/0326000 | A1* | 11/2017 | Heeren | A61F 9/00736 |
| 2017/0354767 | A1* | 12/2017 | Carr | A61M 1/982 |
| 2018/0078159 | A1 | 3/2018 | Edelman et al. | |

FOREIGN PATENT DOCUMENTS

| | | | |
|---|---|---|---|
| WO | 2004065763 | A2 | 8/2004 |
| WO | 2012148750 | A1 | 11/2012 |

* cited by examiner

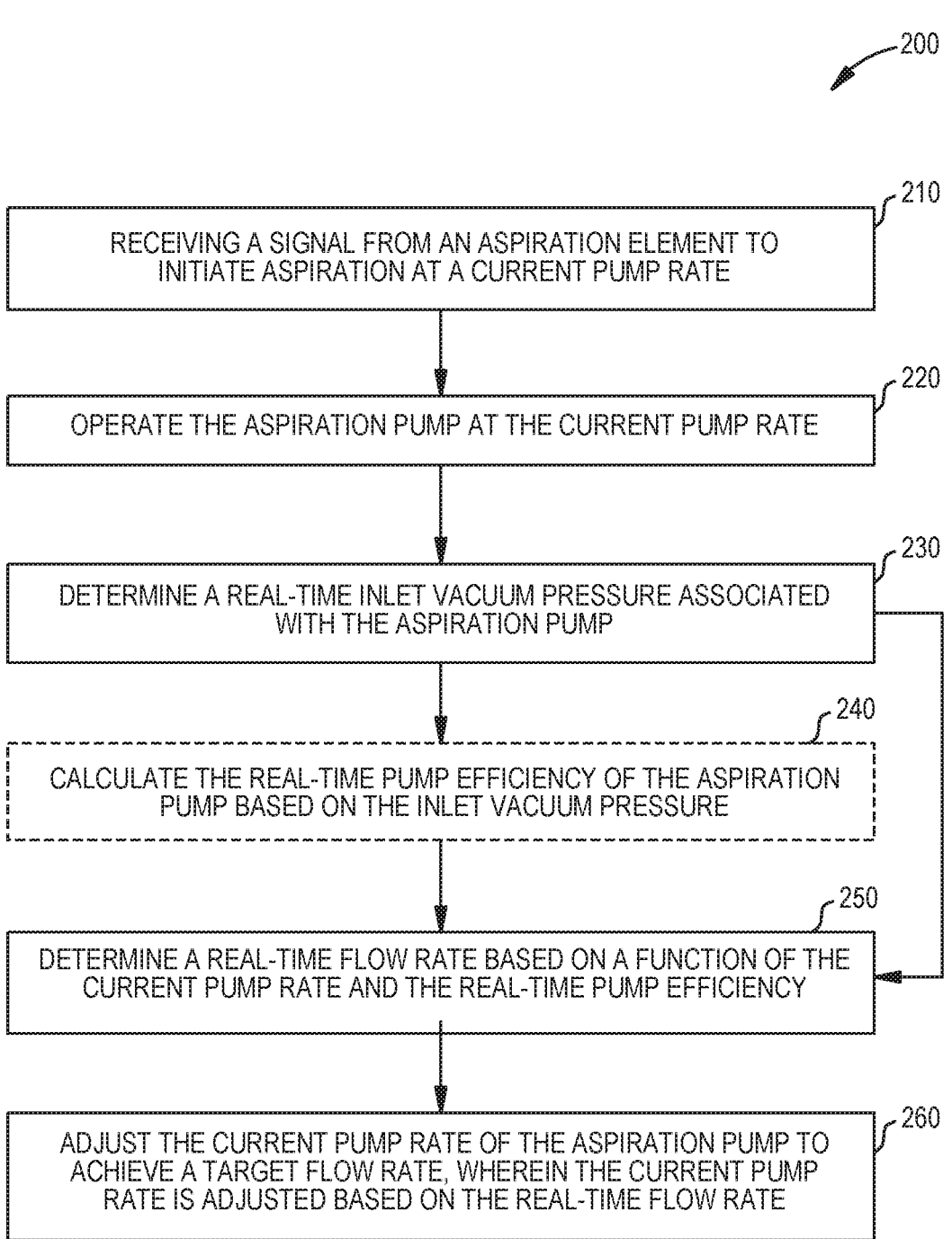

_200_

_210_

RECEIVING A SIGNAL FROM AN ASPIRATION ELEMENT TO INITIATE ASPIRATION AT A CURRENT PUMP RATE

_220_

OPERATE THE ASPIRATION PUMP AT THE CURRENT PUMP RATE

_230_

DETERMINE A REAL-TIME INLET VACUUM PRESSURE ASSOCIATED WITH THE ASPIRATION PUMP

_240_

CALCULATE THE REAL-TIME PUMP EFFICIENCY OF THE ASPIRATION PUMP BASED ON THE INLET VACUUM PRESSURE

_250_

DETERMINE A REAL-TIME FLOW RATE BASED ON A FUNCTION OF THE CURRENT PUMP RATE AND THE REAL-TIME PUMP EFFICIENCY

_260_

ADJUST THE CURRENT PUMP RATE OF THE ASPIRATION PUMP TO ACHIEVE A TARGET FLOW RATE, WHEREIN THE CURRENT PUMP RATE IS ADJUSTED BASED ON THE REAL-TIME FLOW RATE

FIG. 2

METHODS AND SYSTEMS FOR CONTROLLING ASPIRATION FLOW RATE

INTRODUCTION

Aspects of the present disclosure generally relate to methods and systems for controlling aspiration flow rate during an aspiration operation.

During surgical procedures, a surgeon may wish to aspirate certain material out of a body part. In one example, to perform the aspiration, the surgeon places a probe, which is connected to a surgical system through a connector, inside the body part. In such an example, the surgical system comprises an aspiration pump (e.g., peristaltic pump) that operates to create suction or vacuum at the tip of the probe in order to aspirate the material out of the body part.

During an aspiration operation, the surgical system's ability to attract material to the tip of the probe, for purposes of emulsifying and/or aspirating the material out of the body part, is critical. The surgical system's ability to attract material to the tip of the probe may be referred to as followability. In certain cases, in order generate enough followability, the surgical system may increase the pump rate, thereby, increasing aspiration. Excess aspiration, however, may be counter-productive because it can, for example, cause an excessive flow of material through the body part, resulting in turbulence which may in turn reduce followability. Excess aspiration may also damage the body part from which material is being withdrawn. For example, if the body part is a patient's eye, excess aspiration may reduce the eye chamber's stability and damage the patient's vision.

Vacuum rise is also critical during aspiration procedures. Vacuum rise refers to the rate of vacuum increase once an occlusion has been formed at, for example, the tip of the probe. Generally occlusions form because the material that is being aspirated may include not only fluids but also solids. An adequate amount of vacuum rise allows the probe to achieve a better grip on the occluding material prior to emulsifying the material or mechanically breaking it. A higher pump rate naturally results in a faster vacuum rise. However, as described above, a higher-than-necessary pump rate may result in excess aspiration, causing a reduction in followability, which corresponds to a reduction in the surgical system's ability to attract material to the tip of the probe. On the other hand, a pump rate that results in an adequate amount of followability may be less than optimal for achieving the right amount of vacuum rise.

Existing systems that are configured with a fixed pump rate throughout an aspiration operation are suboptimal because they either do not provide enough followability or enough vacuum rise. Other existing systems may be configured to automatically adjust the pump rate upon detecting the onset of an occlusion. Such systems may utilize a discrete threshold-based occlusion onset detection ("DTOOD") mechanism, which samples vacuum pressure periodically and, after detecting that vacuum has risen to a certain point, it determines an occlusion is occurring and, on that basis, increases the pump rate to increase the aspiration flow rate.

There is, however, a lag associated with systems using the DTOOD mechanism, because, as discussed, the system does not engage to increase the pump rate unless vacuum has risen to a certain level. During this lag, the aspiration flow rate falls, resulting in an undesirable performance by the surgical system. Once vacuum reaches a certain point, the DTOOD mechanism may arbitrarily increase the pump rate to a pre-determined speed causing a sudden and unnecessary amount of aspiration. As such, the DTOOD mechanism, in certain cases, provides inconsistent performance. In addition to the reasons discussed above, the DTOOD mechanism is also suboptimal when the surgical system is operated with a low vacuum setting, because vacuum may never rise to the level that is required by the system to initiate engaging and increasing the pump rate.

Also, generally, using the pump rate as a control parameter may not be effective because the actual aspiration flow rate of the material during the aspiration operation may not directly correspond to the pump rate used. For example, a certain pump rate may be expected to result in a certain expected flow rate. However, the expected flow rate and the actual flow rate may only match in certain situations, such as when the flow of the material is unrestricted. In the presence of any restriction, the actual flow may be different (e.g., lower) than the expected flow rate.

BRIEF SUMMARY

The present disclosure relates to methods and systems for controlling aspiration flow rate. Certain embodiments provide a surgical system comprising a pump motor configured to couple to a pump for pumping material through a probe, wherein the probe is connected to the pump through a connector. The surgical system further comprises a control module configured to determine a real-time flow rate through the probe and adjust a current pump rate of the pump to achieve a target flow rate, wherein the current pump rate is adjusted based on the real-time flow rate.

Certain embodiments provide a method of operating a pump, performed by a surgical system, for pumping material through a probe. The method generally includes receiving a signal from an aspiration initiation element to initiate an aspiration pump at a current pump rate for aspirating the material through a probe, wherein the probe is connected to the pump through a connector. The method also includes operating the aspiration pump at the current pump rate. The method also includes determining a real-time flow rate through the probe. The method also includes adjusting the current pump rate of the aspiration pump to achieve a target flow rate, wherein the current pump rate is adjusted based on the real-time flow rate.

Certain embodiments provide a non-transitory computer readable medium having instructions stored thereon that, when executed by a surgical system, cause the surgical system to perform the method described above.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 2 illustrates example operations for controlling the aspiration flow rate during an aspiration operation, in accordance with certain embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure relate generally to methods and systems for controlling the aspiration flow rate. In order to resolve the deficiencies relating to existing solutions, certain embodiments herein describe a surgical system that controls the aspiration flow rate during aspiration operations based on a calculation of the real-time aspiration flow rate.

Figure 1:
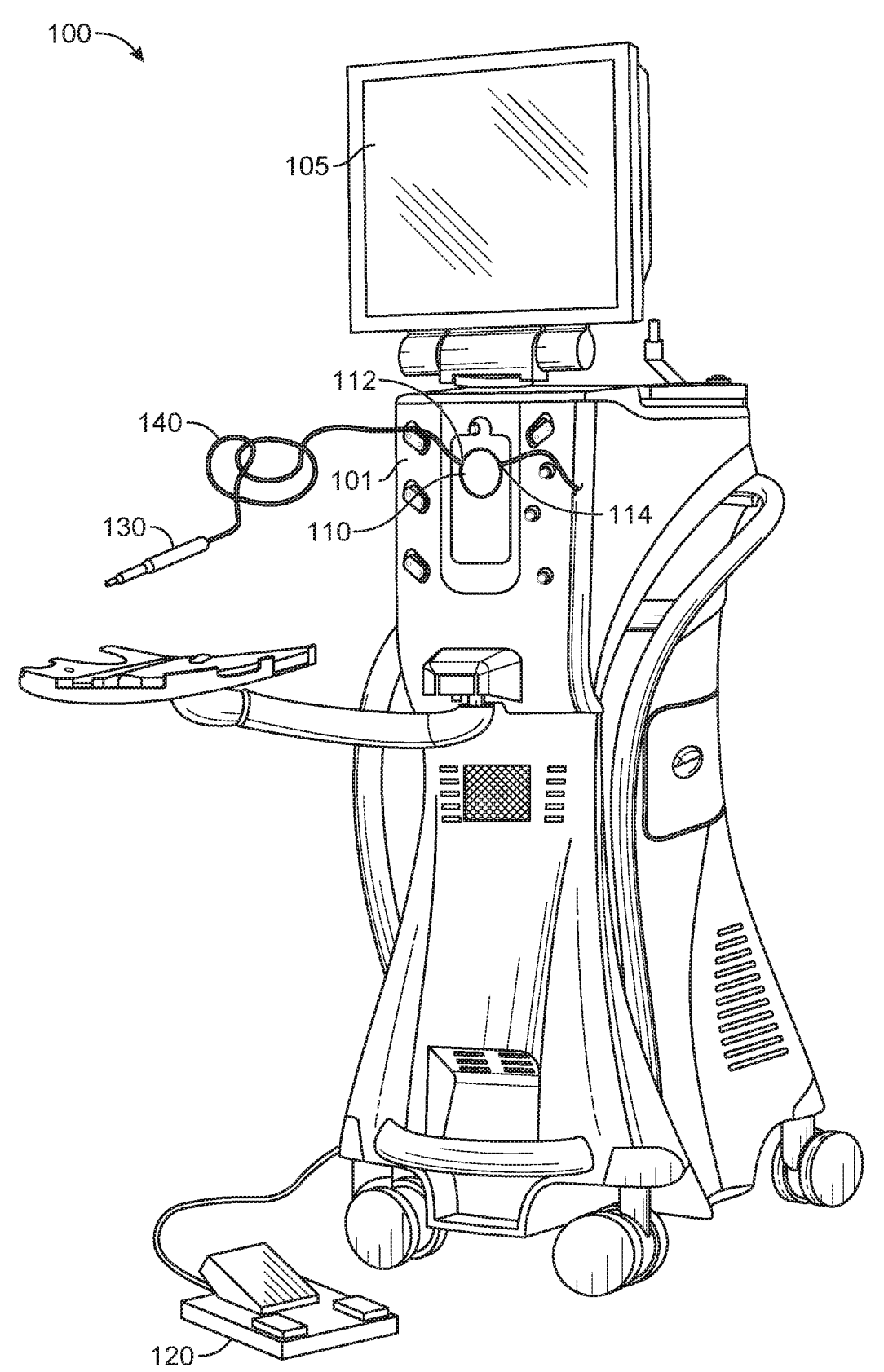
FIG. 1 illustrates an exemplary surgical system that facilitates an operation for aspirating material out of a body part, in accordance with certain embodiments.

FIG. 1 illustrates an exemplary surgical system 100 (e.g., ophthalmic surgical system) that facilitates an operation for aspirating material out of a body part (e.g., patient's eye) of a human or animal through a probe 130. Surgical system 100 comprises a user interface 105, a foot pedal 120, and a control module 101. User interface 105 is used by a user (e.g., surgeon) to provide input to or select a functionality of surgical system 100. Foot pedal 120 is an initiation element used to initiate a functionality, such as an aspiration/irrigation operation, and provide input (e.g., target flow rate) to control module 101. As shown, surgical system 100 is connected to probe 130, which is placed by the user in the body part for the aspiration of the material. Surgical system 100 and probe 130 are connected together via connector 140, which is an elastomer fluid conduit or air tube. At one end, connector 140 is connected to an inlet port 112 of an aspiration pump ("pump") 110 while, at the other end, connector 140 connects to probe 130.

Pump 110 operates to create a vacuum at inlet port 112 which then causes a vacuum at the tip of probe 130, resulting in material being pulled through probe 130 and transported to pump 110. Pump 110 also comprises an outlet 114 through which the material is ejected. In certain aspects, pump 110 is a peristaltic pump that is a part of surgical system 100. In certain aspects, pump 110 is a peristaltic pump that is part of a surgical cassette. The surgical cassette is, in certain aspects, a component that is not a part of surgical system 100. In such aspects, the surgical cassette is placed against a roller head of surgical system 100 that is configured to be rotated by a pump motor within surgical system 100. The operations of a pump motor, such as the pump rate (e.g., corresponding to the rotational speed of the pump measured in rotation per second (RPS)), are controlled by control module 101. An example of a surgical cassette is described in U.S. Pat. No. 8,790,096, whose description of the surgical cassette and the multi-pump segment is incorporated herein by reference. Note that surgical system 100 is configured to operate pump 110 regardless of whether pump 110 is a part of surgical system 100 or if it is a separate component.

Pump 110, in certain aspects, comprises one or more pump segments that are able to engage the rollers of the roller head. Each rotation of the roller head causes a vacuum at inlet port 112 of pump 110, as described above, which results in material being aspirated out of the body part and transported through connector 140 and to pump 110. Therefore, with each rotation, a certain volume of material is ejected from pump 110 through outlet port 114. This volume is referred to as the volume per rotation (VPR) of pump 110. In certain aspects, different pumps may have different VPRs. If a pump, such as the one described in U.S. Pat. No. 8,790,096, is used, then the VPR may refer to a volume of material sealed within the active regions of the pump. The volume of material sealed within these active regions corresponds to the volume of material that is ejected from the pump with each rotation.

As described above, during an aspiration operation, balancing followability and vacuum rise may be important. Balancing followability and vacuum rise at all times results in a relatively desirable and constant aspiration flow rate. As described above, certain existing systems and solutions attempt to strike a balance between followability and vacuum rise by adjusting the pump rate. However, such systems are suboptimal because, for example, they perform pump rate adjustments with a delay, causing undesirable performance.

Accordingly, certain aspects described herein relate to a surgical system (e.g., ophthalmic surgical device) that is configured to control the aspiration flow rate throughout the aspiration operation by periodically calculating the real-time flow rate and adjusting the pump rate based on the real-time flow rate in order to achieve a target flow rate. In certain aspects, the target flow rate may correspond to a desirable balance between followability and vacuum rise. Such a surgical system may reduce delays in adjustment of the pump rate and have improved performance, such as a more constant flow rate. For example, the aspects described herein enable a surgical system to sense any reduction in flow rate prior to a full occlusion and to adjust the pump rate accordingly to maintain the target flow rate.

FIG. 2 illustrates example operations 200 for controlling the aspiration flow rate during an aspiration operation. Operations 200 are described herein by reference to FIG. 1 and its components.

At block 210, control module 101 of surgical system 100 receives a signal from an aspiration initiation element to initiate aspiration at a current pump rate. For example, a user may place probe 130 into a body part (e.g., a patient's eye) or cavity and press foot pedal 120 to initiate the aspiration of material out of the body part. In certain aspects, instead of foot pedal 120, the surgeon may use user interface 105 to initiate the aspiration. Note that although certain aspects described herein relate to aspirating material out of a body part, surgical system 100 may be used for aspirating material out of other objects as well.

At block 220, control module 101 operates the pump at the current pump rate. For example, once control module 101 receives a signal from the aspiration initiation element (e.g., foot pedal 120, user interface 105, etc.), control module 101 begins operating the pump 110 at an initial pump rate. The initial pump rate may be a pre-configured or user-defined pump rate. For example, control module 101 may be configured to initiate aspiration operations during a certain surgical procedure at a certain initial pump rate. In another example, the user may indicate the initial pump rate to control module 101 through the aspiration initiation element. For instance, the user may input the initial pump rate into user interface 105 or indicate the initial pump rate by pressing foot pedal 120.

At block 230, control module 101 determines a real-time inlet vacuum pressure associated with the pump. After control module 101 initiates the aspiration at the initial pump rate, control module 101 is configured to periodically determine the real-time inlet vacuum pressure at pump 110 to calculate the real-time aspiration flow rate. In certain aspects, inlet vacuum pressure refers to the difference in atmospheric pressure and pressure that is sensed at inlet port 112. In aspects where pump 110 is part of a surgical cassette, a pressure sensor (e.g., sensor 317 shown in FIG. 3) may be used to sense the inlet vacuum pressure. The pressure sensor may then indicate the sensed inlet vacuum pressure to control module 101.

In certain aspects, control module 101 is configured to sample or determine the real-time inlet vacuum pressure at pump 110 at certain time increments. As an example, control module 101 may be configured to determine the inlet vacuum pressure at 5 millisecond (ms) time increments. To illustrate this with an example, if control module 101 initiates the aspiration at the initial pump rate at to, control module 101 may determine intlet vacuum pressure at $t_1 = t_0 + 5$ ms. Control module 101 may again determine inlet vacuum pressure at $t_2 = t_1 + 5$ ms, and so on.

At block 240, control module 101 is optionally configured to calculate the real-time pump efficiency of the pump based on the inlet vacuum pressure. Each time control module 101 determines the real-time inlet vacuum pressure, in certain aspects, it calculates a real-time pump efficiency of pump 110. For example, control module 101 may be configured with a pump efficiency function (e.g., $\eta(v)$, where v is the inlet vacuum pressure), associated with pump 110, that uses the inlet vacuum pressure as a parameter to output the pump efficiency of pump 110. Each pump may have a different pump efficiency function. As a result, in certain aspects, surgical system 100 may store pump profiles of various pumps in its non-volatile storage. In such aspects, control module 101 selects a pump profile based on the pump that is being used for the aspiration operations. The pump profile may include a pump efficiency function that can be used by control module 101 to calculate the pump's efficiency using the most recent inlet vacuum pressure.

For example, having determined that pump 110 is being used for aspiration, control module 101 selects the pump profile associated with pump 110 to determine the correct pump efficiency function. Subsequently, using the real-time inlet vacuum pressure vi measured at $t_1$, control module 101 utilizes the pump efficiency function included in a profile of pump 110 to calculate real-time pump efficiency $PE_1$. In certain aspects, surgical system 100 may be configured to only work with one pump. In such aspects, control module 101 may be pre-configured with a pump efficiency function of the pump. As described above, performing block 240 may be optional.

At block 250, control module 101 determines a real-time flow rate based on a function of the current pump rate and the real-time pump efficiency of the pump. In certain aspects, control module 101 is configured with an aspiration flow rate (AFR) function having a number of parameters including one or more of the VPR of pump 110, the pump rate (rounds per second (RPS)), and the pump efficiency ($\eta(v)$). An example of such an AFR function is shown below:

$$AFR = VPR*RPS*\eta(v)$$

In the AFR function above, the aspiration flow rate refers to an estimate of the volume of material that is aspirated by probe 130 per unit of time. VPR, as described above, refers to the volume of material that is ejected from pump 110 through outlet port 114. Different pumps may have different VPRs. In certain aspects, surgical device 100 is configured with the VPR of the pump that is being used for aspiration. For example, the VPR of pump 110 may be included in pump 110's pump profile stored in surgical system 100's storage (e.g., storage 304 of FIG. 3). In such an example, by retrieving pump 110's profile, control module 101 is able to determine the corresponding VPR. In certain aspects, surgical system 100 may be configured to only work with one pump. In such aspects, control module 101 may be pre-configured with VPR of the pump.

The AFR function above also comprises RPS, which is a measure of the speed of pump 110's pump motor or the pump rate. In order to calculate the real-time flow rate at a given time, control module 101 is configured to use the pump rate at that time, which is referred to as the current pump rate. For example, at $t_1$, control module 101 utilizes the current pump rate at $t_1$ to calculate the real-time AFR. In the example above, the current pump rate at $t_1$ is the same as the initial pump rate that control module 101 initiated the aspiration operation with.

In the AFR function above, $\eta(v)$ refers to pump 110's efficiency. In certain aspects, control module 101 utilizes the real-time pump efficiency calculated at optional block 240. Having the VPR, the current RPS, and the real-time pump efficiency, control module 101 is then able to calculate the real-time AFR.

In the aspects described above, control module 101 is configured to calculate the real-time pump efficiency, determine pump 110's VPR, and then utilize the calculated pump efficiency and the determined VPR to calculate the real-time AFR using the AFR function. However, in certain aspects, the AFR function described above is pump-specific such that each pump may have a different AFR function. A pump-specific AFR function already incorporates the corresponding pump's VPR and pump efficiency function. In such aspects, control module 101 is, therefore, able to use the inlet vacuum pressure, determined at step 230, as well as the current RPS as input into the pump-specific AFR function to calculate the real-time AFR. As a result, in such aspects, control module 101 does not separately calculate the real-time pump efficiency of pump 110 and/or determine pump 110's VPR. In certain aspects, control module 101 is configured with pump 110's pump-specific AFR function. For example, pump 110's pump-specific AFR function may be stored in surgical system 100's storage and retrieved by control module 101 when calculating the real-time AFR. In certain aspects, if surgical system 100 is able to work with different pumps, such as pump 110, control module 101 may be configured to identify the profile of the pump that is being used for aspiration and retrieve the corresponding pump's AFR function from the profile.

At block 260, control module 101 adjusts the current pump rate of the pump to achieve a target flow rate wherein the current pump rate is adjusted based on the real-time flow rate. Having determined the real-time AFR, control module 101 may be configured to adjust the current pump rate using any of a number of different techniques.

In certain embodiments, control module 101 is configured to compare the calculated real-time AFR and a target flow rate. In certain aspects, a user may input the target flow rate through user interface 105. In certain aspects, the user may input and/or adjust the target flow rate using foot pedal 120. In certain aspects, control module 101 is pre-configured with the target flow rate. For example, a user may select the type of procedure they are about to perform by interacting with user interface 105. Based on the user selection, control module 101 may be configured to determine the target flow rate corresponding to that procedure.

If the real-time AFR is not within a threshold of the target AFR, then control module 101 is configured to calculate a target pump rate that corresponds to the target flow rate. As an example, if the real-time AFR and the target AFR are within a certain percentage or decimal point value of each other, control module 101 may determine that the pump is operating at a desirable pump rate and, therefore, skip any adjustment of the pump rate until the next time increment when the real-time AFR is calculated again. In certain other aspects, however, the threshold is defined such that if the real-time AFR and the target AFR are not exactly the same, control module 101 is configured to calculate a target pump rate to achieve the exact target AFR.

When calculating a target pump rate, control module 101 is configured to use the same AFR function that was used to calculate the real-time AFR. For example, control module 101 may use the example AFR function below:

$$AFR=VPR*RPS*\eta(v)$$

When calculating the target pump rate, the input to the AFR function above includes the target AFR, the VPR, and the pump efficiency, while the output is the target pump rate (RMP). For example, if the real-time AFR is 0.5 cc/s, the VPR is 1 cc and the pump efficiency is 70%, then the target pump rate or RPS equals (0.5 cc/s)/(1 cc*70%). As described above, in certain aspects, pump efficiency may be determined (as described in relation to block 240) prior to the calculation of the real-time AFR. In some other aspects, pump efficiency may be determined when control module 101 determines to calculate target RPS.

In other embodiments, control module 101 is configured to calculate the target pump rate based on the difference between the real-time AFR and the target AFR. For example, based on the difference between the real-time AFR and the target AFR, control module 101 may be configured to calculate an amount to change the current pump rate to achieve the target flow rate. In certain aspects, control module 101 is configured with a proportional integral derivative (PID) controller mechanism that allows control module 101 to determine by how much the current pump rate should be changed to achieve the target flow rate based on the different between the real-time AFR and the target AFR.

Once a target pump rate (or an amount by which to change the current pump rate) is calculated (using any suitable technique such as those described herein), control module 101 changes the current pump rate to the target pump rate (or changes the current pump rate by the calculated amount). By repeating steps 230 through 260 of operations 200 periodically (e.g., every 5 ms), control module 101 is able to continuously adjust the current pump rate based on the real-time AFR. Adjusting the current pump rate based on the real-time AFR enables control module 101 to control the AFR by achieving and maintaining the target flow rate during the aspiration operation.

Figure 3:
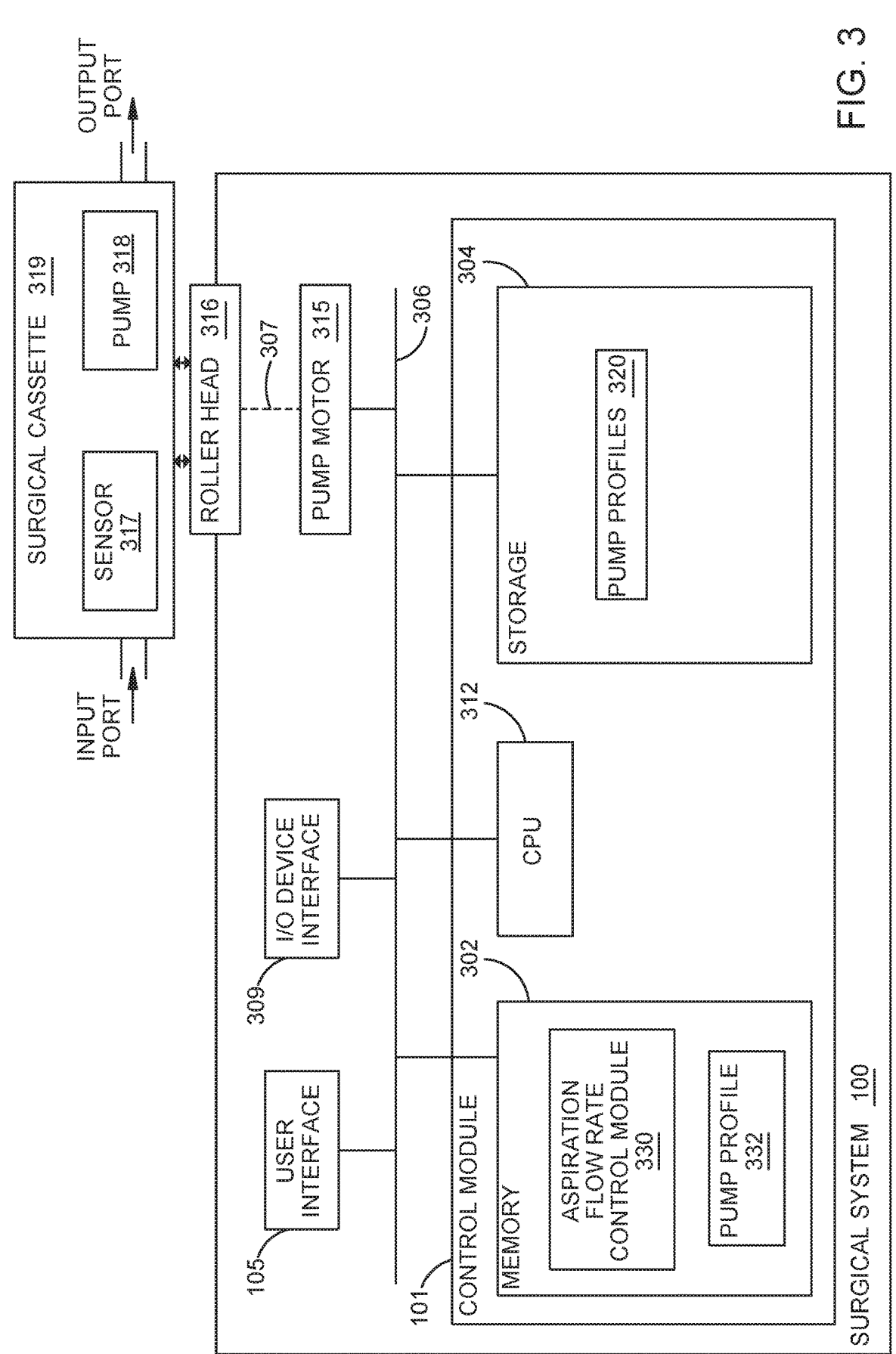
FIG. 3 illustrates exemplary components of the surgical system of FIG. 1, in accordance with certain embodiments.

FIG. 3 illustrates an exemplary diagram showing how the various components of the surgical system 100 of FIG. 1 communicate and operate together. As shown, surgical system 100 includes, without limitation, control module 101, user interface display 105, an interconnect 306, pump motor 315, roller head 316, and at least one I/O device interface 309, which may allow for the connection of various I/O devices (e.g., keyboards, displays, mouse devices, pen input, etc.) to surgical system 100. FIG. 3 also shows surgical cassette 319, which includes pump 318 (e.g., shown as pump 110 in FIG. 1) and sensor 317. Surgical cassette 319 is a separate component that is capable of being coupled to surgical system 100 such that the pump segments of pump 318 are able to engage the rollers of roller head 316. As shown, surgical cassette 319 comprises an input port through which material enters surgical cassette 319. Using sensor 317, surgical cassette 319 then measures the inlet vacuum pressure. The material is then pumped through pump 318 and ejected from surgical cassette 319's output port.

Control module 101 includes a central processing unit (CPU) 312, a memory 302, and storage 304. CPU 312 may retrieve and execute programming instructions stored in the memory 202. Similarly, CPU 312 may retrieve and store application data residing in memory 202. Interconnect 306 transmits programming instructions and application data, among CPU 312, I/O device interface 309, user interface 105, memory 302, storage 304, pump motor 315, etc. CPU 312 can represent a single CPU, multiple CPUs, a single CPU having multiple processing cores, and the like. Additionally, memory 302 represents a volatile memory, such as a random access memory. Furthermore, the storage 304 represents a non-volatile memory, such as a disk drive. Although shown as a single unit, storage 304 may be a combination of fixed or removable storage devices, such as fixed disc drives, removable memory cards or optical storage, network attached storage (NAS), or a storage area-network (SAN).

As shown, storage 304 includes pump profiles 320 of various pumps, such as pump 318. Memory 302 includes an AFR control module 330 for controlling the aspiration flow rate of during aspiration operations, as described in the embodiments herein (e.g., operations 200 of FIG. 2). In addition, memory 302 includes a pump profile 332 of a pump (e.g., pump 318) being used for aspiration. For example, once the control module 101 determines the pump that is being used for aspiration (e.g., through user input via user interface 105), control module 101 retrieves the pump's profile 332 from storage 304 and uses the information indicated in pump profile 332 during the aspiration operations. In such an example, AFR module 330 comprises executable instructions for controlling the aspiration flow rate based on pump profile 332 of pump 318, the real-time AFR, and the target AFR, according to the embodiments described herein.

In FIG. 3, because more than one pump can be used for the aspiration, surgical system 100 is configured with pump profiles 320 from which control module 101 retrieves the pump profile (e.g., pump profile 332) that is being used to periodically determine the pump efficiency when calculating the real-time AFR, as described above. However, in certain aspects, only one type of pump may be used with surgical system 100. In such aspects, surgical system 100 is not configured with pump profiles 320 of various pumps. In such aspects, AFR control module 330 may be pre-configured with information about the pump being used. For example, AFR control module 330 may comprise the pump efficiency function of the pump, the volume per rotation of the pump, and/or the pump-specific AFR function of the pump.

As shown, surgical system 100 also includes pump motor 315. Pump motor 315 is configured to couple to pump 318 for engaging or operating pump 318. Pump motor 315 operates pump 318 by, for example, rotating roller head 316 at a pump rate indicated by control module 101. Pump motor 315 may be an actuator that receives control signals from control module 101. Pump motor 315 and roller head 316 are connected through mechanism 307, which may be a mechanical mechanism. For example, mechanism 307 may be a motor shaft that rotates roller head 316. Although in FIG. 3 the pump 318 is not part of surgical system 100 and is instead a part of surgical cassette 319, in certain other aspects the pump is a part of surgical system 100.

Although the methods and operations above were described in relation to maintaining the target flow rate during aspiration operations, one of ordinary skill in the art appreciates that the same methods and operations are similarly applicable to maintaining the target flow rate during irrigation operations. More specifically, surgical system 100 may be configured to control the irrigation flow rate (IFR) throughout an irrigation operation by periodically calculating the real-time flow rate and adjusting the pump rate based on the real-time flow rate in order to achieve a target flow rate. For example, control module 101 of surgical system 100 may periodically calculate the real-time flow rate by periodically sampling the outlet pressure (i.e., the pressure with which material is irrigated out of surgical system 100 and into the surgical site or body part) using a sensor similar to sensor 317.

Note that when surgical system 100 is used for irrigation, surgical cassette 319 may use separate input and output ports for irrigation (e.g., not the same input and output ports used for aspiration, as shown in FIG. 3). For example, material may flow from an input port into surgical cassette 319 and be received by an irrigation pump (e.g., pump 318), which then pumps the material out from an output port of surgical cassette 319. The outlet pressure of the material is sensed by a sensor after the material leaves the irrigation pump and is on its way out to the output port. In other words, unlike for aspiration where the pressure of the material is first sensed by sensor 317 before the material is pumped by pump 318, for irrigation, the material is first pumped by an irrigation pump before its outlet pressure is sensed by a sensor.

Outlet pressure is denoted by "o" below. Using the sampled outlet pressure, control module 101 may then calculate real-time pump efficiency for the irrigation pump (e.g., pump 110, pump 318, etc.) that is performing the irrigation. The pump efficiency for an irrigation pump can be calculated similar to how an aspiration pump's efficiency is calculated, as described above. For example, control module 101 may be configured with the pump efficiency function of the irrigation pump for calculating the pump efficiency using the most recent sampled outlet pressure.

Once the irrigation pump's efficiency is calculated, control module 101 may use the flow rate function described in relation to block 250 of FIG. 2 to calculate the real-time flow rate. For example, control module 101 uses the function $IFR=VPR*RPS*\eta(o)$. By calculating the real-time flow rate, control module 101 is then able to adjust the current pump rate of the irrigation pump to achieve a target flow rate, similar to the operations described in relation to block 260 of FIG. 2.

Note that the aspects described herein may be implemented within a surgical system surgical system 100) for performing eye surgeries. In such cases, when the surgical system is used for aspiration; the material aspirated out of a patient's eye may include fluids, OVDs (Ophthalmic Viscoelastic Devices), or pieces of emulsified lens fragments. When the surgical system is used for irrigation, however, the material may include irrigation solutions.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A surgical system comprising:
   a pump motor configured to couple to a pump for pumping material through a probe, wherein the probe is connected to the pump through a connector; and
   a control module configured to:
      initiate operation of the pump at an initial pump rate;
      determine a real-time inlet vacuum pressure associated with the pump;
      determine a real-time pump efficiency of the pump based on the real-time inlet vacuum pressure;
      determine a real-time flow rate through the probe based on a function of the initial pump rate, the real-time pump efficiency of the pump, and a volume per rotation of the pump; and
      adjust the initial pump rate of the pump to achieve a target flow rate,
      wherein the initial pump rate is adjusted based on the real-time flow rate.

2. The surgical system of claim 1, wherein the control module being configured to determine the real-time flow rate through the probe comprises the control module being configured to:
   receive a signal from an initiation element to initiate operation of the pump at the initial pump rate; and
   operate the pump at the initial pump rate.

3. The surgical system of claim 2, wherein:
   the pump is an aspiration pump for aspirating the material through the probe.

4. The surgical system of claim 1, wherein the volume per rotation corresponds to a volume of material sealed within an active region of the pump.

5. The surgical system of claim 1, wherein the control module being configured to adjust the initial pump rate of the pump comprises the control module being configured to:

compare the real-time flow rate and the target flow rate;

upon determining that the real-time flow rate and the target flow rate are not within a threshold of each other, calculate a target pump rate based on a function of the real-time pump efficiency and the target flow rate; and change the initial pump rate of the pump to the calculated target pump rate.

6. The surgical system of claim 1, wherein the control module being configured to adjust the initial pump rate of the pump comprises the control module being configured to:

calculate an amount to change the initial pump rate to achieve the target flow rate based on a difference between the real-time flow rate and the target flow rate; and change the initial pump rate of the pump by the calculated amount.

7. The surgical system of claim 1, wherein the control module is further configured to keep the target flow rate constant during an operation of the pump.

8. The surgical system of claim 1, wherein the real-time inlet vacuum pressure associated with the pump is determined utilizing a sensor in a surgical cassette coupled to the pump.

9. The surgical system of claim 1, wherein the control module being configured to adjust the initial pump rate comprises the control module being configured to:

determine a target pump rate based on the function used to determine the real-time flow rate.

10. A method of operating a pump, performed by a surgical system, for pumping material through a probe, comprising:

receiving a signal from an initiation element to initiate operation of the pump at an initial pump rate for pumping the material through the probe, wherein the probe is connected to the pump through a connector;

operating the pump at the initial pump rate;

determining a real-time inlet vacuum pressure associated with the pump;

determining a real-time pump efficiency of the pump based on the real-time inlet vacuum pressure;

determining a real-time flow rate through the probe based on a function of the initial pump rate, the real-time pump efficiency of the pump, and a volume per rotation of the pump; and adjusting the initial pump rate of the pump to achieve a target flow rate, wherein the initial pump rate is adjusted based on the real-time flow rate.

11. The method of claim 10, wherein:

the pump is an aspiration pump for aspirating the material through the probe.

12. The surgical system of claim 10, wherein the volume per rotation corresponds to a volume of material sealed within an active region of the pump.

13. The method of claim 10, wherein adjusting the initial pump rate comprises: comparing the real-time flow rate and the target flow rate;

upon determining that the real-time flow rate and the target flow rate are not within a threshold of each other, calculating a target pump rate based on a function of the real-time pump efficiency of the pump and the target flow rate; and changing the initial pump rate of the pump to the calculated target pump rate.

14. The method of claim 10, wherein adjusting the initial pump rate comprises:

calculating an amount to change the current initial pump rate to achieve the target flow rate based on a difference between the real-time flow rate and the target flow rate; and changing the initial pump rate of the pump by the calculated amount.

15. The method of claim 10, wherein the adjusting further comprises:

keeping the target flow rate constant during the operation of the pump.

16. The method of claim 10, wherein the real-time inlet vacuum pressure associated with the pump is determined utilizing a sensor in a surgical cassette coupled to the pump.

17. The method of claim 10, wherein adjusting the initial pump rate of the pump to achieve the target flow rate comprises:

determining a target pump rate based on the function used to determine the real-time flow rate.

18. A non-transitory computer readable medium having instructions stored thereon that, when executed by a surgical system, cause the surgical system to perform a method comprising:

receiving a signal from an initiation element to initiate operation of a pump at an initial pump rate for pumping material through a probe, wherein the probe is connected to the pump through a connector;

operating the pump at the initial pump rate;

determining a real-time inlet vacuum pressure associated with the pump;

determining a real-time pump efficiency of the pump based on the real-time inlet vacuum pressure;

determining a real-time flow rate through the probe based on a function of the initial pump rate, the real-time pump efficiency of the pump, and a volume per rotation of the pump; and adjusting the initial pump rate of the pump to achieve a target flow rate, wherein the initial pump rate is adjusted based on the real-time flow rate.

19. The non-transitory computer readable medium of claim 18, wherein the real-time inlet vacuum pressure associated with the pump is determined utilizing a sensor in a surgical cassette coupled to the pump.

20. The non-transitory computer readable medium of claim 18, wherein the surgical system is further configured to execute the instructions to adjust the initial pump rate of the pump to achieve the target flow rate by:

determining a target pump rate based on the function used to determine the real-time flow rate.

* * * * *